US006852327B1

(12) United States Patent
Esteban Duran et al.

(10) Patent No.: US 6,852,327 B1
(45) Date of Patent: Feb. 8, 2005

(54) COMPOSITION ATTRACTING INSECTS PERTAINING TO THE COLEOPTERA FAMILY AND USE THEREOF IN THE CONTROL OF PLAGUES IN PALM-TREES AND RELATED PLANTS

(75) Inventors: José Rafael Esteban Duran, Madrid (ES); José Luis Tadeo Lluch, Madrid (ES); Francisco Beitia Crespo, Leganés (ES); Antonio Jimenez Alvarez, Madrid (ES); Consuelo Sanchez-Brunete Palop, Madrid (ES)

(73) Assignee: Instituto Nacional de Investigacion y Tecnologia Agraria y Alimentaria (INIA) (ES)

( * ) Notice: Subject to any disclaimer, the term of this patent is extended or adjusted under 35 U.S.C. 154(b) by 0 days.

(21) Appl. No.: 09/508,031

(22) PCT Filed: Sep. 4, 1998

(86) PCT No.: PCT/ES98/00243

§ 371 (c)(1),
(2), (4) Date: Apr. 26, 2000

(87) PCT Pub. No.: WO99/12425

PCT Pub. Date: Mar. 18, 1999

(51) Int. Cl.$^7$ ............................................... A61K 35/78
(52) U.S. Cl. ...................... 424/405; 424/410; 424/725; 514/724; 514/731
(58) Field of Search ................................ 424/405, 410, 424/725; 514/724, 731

(56) References Cited

PUBLICATIONS

Nagnan et al. (Oleagineux (1992), vol. 47, No. 3, pp. 135–142.*
Umano et al. J. Agric. Food Chem. (1992), vol. 40, No. 4, pp. 599–603.*

"Optimization of Semiochemical–Based Trapping of Metamusius Hemipterus Sericeus (Olivier) (Coleoptera: Curculionidae)"; *Journal of Chemical Ecology*; vol. 22, No. 8; 1996; Robin M. Gilbin–Davis, et al.; pp. 1389–1410.
"Chemical Ecology of the Palm Weevil Rhynchophorus palmarion (L.) (Coleoptera: Curculionidae): Attraction to Host Plants and to a Male–Produced Aggregation Pheromone"; K. Jaffe, et al.; *Journal of Chemical Ecology*; vol. 19, No. 8; 1993; pp. 1703–1720.
"Ethyl Propionate: Synergistic Kairomone for African Palm Weevil, Rhynchophorus phoenicis L. (Coleoptera: Curculionidae)"; Gerhard Gries, et al.; *Journal of Chemical Ecology*; vol. 20, No. 4; 1994; pp. 889–897.
"Field Response of Rhynchophorus Cruentatus (Coleoptera: Curculionidae) to its Aggregation Pheromone and Fermenting Plant Volatiles"; Robin M. Giblin–Davis, et al.; *Florida Entomologist*; 77(1); Mar. 1994; pp. 164–177.
"Chemical and Behavioral Ecology of Palm Weevils (Curculionidae: Rhynchophorinae)"; R. M. Giblin–Davis, et al; *Florida Entomologist*; 79(2); Jun. 1996; pp. 153–167.

* cited by examiner

*Primary Examiner*—Francisco Prats
*Assistant Examiner*—Susan D. Coe
(74) *Attorney, Agent, or Firm*—Ostrolenk, Faber, Gerb & Soffen, LLP

(57) ABSTRACT

The invention is a composition and a method for agriculture. The composition is a semisynthetic mixture (a) which includes (1) an organic compound which is essentially emitted in the fermentation of vegetable parts of the palm tree or related plant, (2) a vegetable material obtained from the palm tree or related plant and which has been ground, fermented, and stabilized, and (3) an organic compound emitted in minor quantity during the fermentation of the vegetable parts of the palm tree or related plant; and (b) a pheromone which is appropriate to control for the target insect. The method includes the application of the composition to a plantation of palm trees and related plants to be protected.

1 Claim, No Drawings

US 6,852,327 B1

COMPOSITION ATTRACTING INSECTS PERTAINING TO THE COLEOPTERA FAMILY AND USE THEREOF IN THE CONTROL OF PLAGUES IN PALM-TREES AND RELATED PLANTS

FIELD OF THE INVENTION

This invention relates to compositions for attracting insects pertaining to the Coleoptera order, and are formed by a semi-synthetic combination comprising chemical products emitted from the natural fermentation of plants and fermented vegetal products, in addition to feromones that are adequate for the insect to be controlled, and also to the use of said attractive compositions in a method designed for pest controlling said insects in palm trees and related plants

BACKGROUND OF THE INVENTION

The various uses of vegetal product derivinq from palmaceous plants and its various species (palm oil, coconut oil, coconuts, dates, etc.) are presently suffering considerable losses as a result insects attacks on plantation areas, mainly in equatorial, tropical, subtropical and/or warm areas of the planet.

The insects which mainly attack palm trees belong to the Coleoptera Curculionidae order, *Rhynchophorinae,* and the *Oxyctes, Scapanes* and, mainly, *Rhynchophorus genera.* Particularly, the *Rhynchophorus palmarnum* and *Rhynchophorus ferrugineus* species are curculionids which constitute a very serious pest affecting palm trees in humid equatorial and tropical zones of the globe. Recently, the *R. ferrugineus* species affecting date palms in the Middle East and Northern Africa has been detected in ornamental palm trees in the Málaga and Granada coast.

Numerous studies reveal that one of the few valid and efficient insect pest control methods available, particularly for preventing the insects natural expansion, consists in its mass-trapping.

In the case of curculionid pests affecting palm trees, the only prospective and/or control methods which have proven to be effective are based on the capture of adult insects of virtually damaging species both as a prognosis and a direct control method through mass-trapping. These methods use a vegetal bait combined with the added feromone of each species to be controlled. However, the ecology itself of the plantation environments provide for limited effectivity of said vegetal baits, in view that, under the best circumstances, bait life rarely exceeds 15 days, and it is therefore necessary to constantly replace the bait and to overcome operational difficulties which complicate the treatment and render it more ave. Moreover, vegetal baits provide irregular results because of the heterogeneity of the vegetal substance in the fermentation.

Thus, the need exists for other insert pest control methods based on the use of baits designed to attract insects that will overcome these inconveniences.

The invention provides a solution to this need based on the use of a composition attractive to insects formed of a semisynthetic combination comprising chemical products emitted from vegetal fermentation, in a natural manner, and from ground, mixed portions of the plants proper.

Therefore, an object of this invention consists in providing a semisynthetic mixture or combination comprising at least one organic compound emitted during the fermentation of vegetable portions of palm trees and related plants and a ground, fermented vegetal matter taken from said plants. The procedure for obtaining the mixture constitutes an additional object of the invention.

Another object of this invention consists in providing a composition attractive to insects that is appropriate for controlling pests of insects, pertaining to the Coleoptera order, in palm trees and related plants, comprising the above mentioned semisynthetic mixture and a feromone corresponding to the insect to be controlled. The procedure for obtaining said composition constitutes a further object of the invention.

Finally, another object of this invention consists in providing a method for controlling pests of insects pertaining to the Coleoptera order, in palm trees and related plants, which includes the use of said compositions that attract insects.

DETAILED DESCRIPTION OF THE INVENTION

The invention provides adequate mixtures for producing compositions that are attractive to insects and prove useful for controlling pests of insects pertaining to the Coleoptera order in palm trees and related plants. In the sense used in this description, the term "palm trees and/or related plants" includes all types and species of palm trees in addition to related plants such as sugar cane, banana trees and agaves.

Mixture (a) provided by the present invention comprises the following components:

(a1) an organic compound selected from the group of compounds providing the main fermentation emission from vegetal portions of the palm tree or related plant; and (a2) a vegetal matter comprising vegetal portions from the palm tree or related plant that, is ground, fermented and stabilized with a preserving agent.

Mixture (a) may also optionally contain a component (a3) selected from the group of compounds forming the lesser emission from the fermentation of vegetal portions of the palm tree or related plant.

component (a1) is an organic compound selected from the group of compounds comprising the main emission from the fermentation of vegetal portions of the plant in question, as chromatographically detected in the natural fermentation of said vegetal matter. Generally, in the case of palm trees, sugar cane, banana trees and agaves, the compounds included in said main emission are organic compounds selected among alcohols, such as methanol and ethanol, and esters, such as ethyl acetate. Therefore; in a particular embodiment of this invention, said component (a1) is selected from the group formed by methanol, ethanol, ethyl acetate and its mixtures. Component (a1) may be present in an amount between 15% and 85% by weight of the total mixture, preferably between 70% and 80% thereof.

Compound (a2) is, a vegetal matter comprising vegetal portion of the plant which are ground, fermented and stabilized with a preserving agent. The vegetal portions liable to be used are the stem, leaves and fruits of the plants in question (palm trees, sugar cane, banana trees or agaves). The vegetal portions used are crushed and milled, are allowed to ferment naturally for an adequate period of time and are then stabilized with an appropriate preserving agent, e.g. ascorbic acid, nitric acid or similar. Thus, in a particular embodiment of this invention, component (a2) is selected from the group formed by stems, leaves, fruits and mixtures thereof from palm trees, sugar cane, banana trees or agaves that are ground, allowed to ferment naturally and stabilized with a preserving agent selected. between ascorbic acid, nitric acid and its mixtures. Component (a2) may be present in mixture (a) in an amount between 15% and 85% by weight of the total mixture, preferably between 19% and 29% thereof. The preserving agent present in component (a2) is found in an amount appropriate for performing its function.

Compound (a3) is an organic compound selected from the group of compounds forming the lesser emission from the fermentation of vegetal portions of the plant in question, chromatographically detected in the natural fermentation of said vegetal matter. These minority compounds are of a varied nature and chemical composition; however, in general, in the, case of palm trees, sugar cane, banana trees and agaves, the compounds included in said lesser emissions include, among numerous other compounds, isobutyl acetate, acetoin, phenol, guaiacol, menthol and 2-phenylethanol. Therefore, in a particular embodiment of this invention, said component (a3) is selected from the group formed by acetoin, phenols guaiacol, 2-phenylethanol and mixtures thereof. Component (a3) may be present in said mixture in an amount between 0 and 2% by weight of the total mixture, preferably between 1 and 5% thereof. Component (a3) enhances, according to the ecosystem involved, the attraction of one or another species of insects in response to a common aggregation feromone.

Mixture (a) may be obtained through a procedure comprising the general stages of preparing componet (a2) and mixing it with component (a1), and optionally with component (a3).

The preparation of component (a2) may be readily conducted at ambient temperature, namely 18 to 25° C., by first grinding and mixing the vegetal portions being used, e.g. stems, leaves and fruits, subsequently spreading the mixture over plates made from an inert material such as stainless steel, glass o neutral plastics, and allowing it to ferment at a temperature ranging from 20 to 25° C. for a period of time ranging from 24 to 48 hours. The mixture obtained is then stabilized with an adequate preserving agent, such as ascorbic acid, citric acid and/or mixtures thereof, to obtain component (a2).

To the component (a2) thus obtained is added component (a1)—e.g. an organic solvent selected between methanol, ethanol, ethyl acetate and mixtures thereof—and, optionally, if so desired, component (a3). After adding these components, the resulting combination is stirred evenly for an adequate period of time, normally under 60 minutes, to obtain mixture (a). This mixture (a) may then be used for preparing a composition that attracts insects, or, if so desired, is placed inside appropriate containers, such as hermetic containers, and preserved in a refrigerator or freezer until such time as they are needed.

These mixtures (a), or so-called "semisynthetic combinations" because they are obtained from natural products (vegetal portions) and chemical products, are appropriate for producing compositions which attract insects pertaining to the Coleoptera order in plantations selected from the group formed by all types and species of palm trees, sugar cane plantations, banana trees, agave zones and mixtures thereof.

The insect-attracting compositions, or so-called semisynthetic baits, provided by this invention comprise the following component:

(a1) a mixture including
   (a1) an organic compound selected from the group of compounds providing the main fermentation emission from vegetal portions of the plant in question;
   (a2) a vegetal matter comprising vegetal portions from the plant in question that is ground, fermented and stabilized with a preserving agent; and optionally
   (a3) an organic compound selected from the group of compounds providing the lesser emission from the fermentation of vegetal portions of the plant in question: and
(b) a feromone corresponding to the insect the pest of which is intended to be controlled.

Mixture (a) and its components (a1), (a2) and (a3) have been previously defined.

Component. (b) is a feromone corresponding to the insect the pest of which is intended to be controlled. This feromone may be a synthetic feromone, preferably a synthetic sexual feromone pertaining to the species of insect the pest of which is intended to be controlled, e.g. Rhynchophorol, a synthetic feromone useful for controlling insects of the *Rhynchophorus* genus. Synthetic feromones, the synthesis of which can be achieved through conventional chemical means, are known, commercially available products. Component (b) may be present in the attracting composition provided by this invention in an appropriate quantity.

The attracting compositions of the invention present a liquid consistency and leave and leave a steady sediment on the bottom of the container used for the application which gradually delivers the precise components to the composition, as required for the latter to remain active and maintain the desired attraction properties.

The procedure for fabricating the insect attracting composition provided by this invention comprises the stages of preparing the mixture (a) and loading said mixture with the corresponding feromone. The preparation of mixture (a) has been previously described. Loading of the feromone may be perform by conventional methods which normally comprise placing mixture (a) in contact with the feromone in their liquid phase.

The insect attracting composition of this invention is suitable for controlling insect pests in plants; it is particularly suitable for controlling insects pertaining to the Coleoptera order and embraces virtually all Rhynchophorinae, in addition to *Metamassius* sp., *Scapanes* sp., Oryctessp., etc., in all types and species of palm trees, in mixed or non-mixed sugar cane and banana tree plantation, and in agave areas.

Thus, the invention also provides a method for controlling insect pests, particularly for controlling insects pertaining to the Coleoptera order in all types and species of palm trees, in mixed or non-mixed sugar cane and banana tree plantations and in agave areas, involving the use of the insect attracting composition provided by this invention. More specifically, the method for controlling insect pests comprises applying a suitable amount of said insect attracting composition, loaded wish the corresponding feromone based on the insect the pest of which is intended to be controlled, on the grove intended to be protected.

In the sense used in this description, the term "insect pest control" includes detecting and fighting said insects.

Applied as a prognosis (detection) method, one trap (with semisynthetic bait and its corresponding feromone) may be installed for every 4 or 5 hectares, although the local experts will always be required to establish the most adequate density based on the species of; insects being acted against.

By using the mass-trapping method of fighting against species which so allow, trap density call for installing at least one trap per hectare, obviously based on the opinion of the experts and the species of insects to be trapped.

The insect attracting composition maybe applied through conventional methods and with the use of conventional equipment and devices applied to normal insect pest handling and control methods, particularly involving devises used for applying vegetable baits. Alternatively, disperser systems may be used comprising a material capable of absorbing or adsorbing the insect attracting composition of the invention and progressively releasing it, optionally enveloped by a hydrosoluble film.

When using the insect attracting composition of the invention, it is most important that, while in the storage containers and prior to loading the spreaders, the composition is thoroughly stirred to enable all liquid and semisolid (sediment) compounds comprised in the insect attracting composition of the invention to be homogeneously incorporated to each spreader, thus allowing the sediment to gradually release the minority compounds, i.e. compound (a3), from the fermentation of the treated vegetal portions discontinued as a result of the cold storage but which nonetheless is slowly resumed as the composition is being used.

Tests conducted in French Guiana against *Rhynchophorus palmarum* and in Spain against *Rhynchophorus ferrugineus* Olivier using suitable insect attracting compositions of the Invention with their respective aggregation feromones have provided far better results than those of normally utilized vegetal baits (sugar cane and/or palm tree medulla fermented during 24–48 hours). During the first week of use, the performance of the inventive compositions reflects an average efficiency of 120% in respect to the vegetal reference specimen, a value which is distinctively higher, however, as from the seventh day and up to the thirtieth day (a 1-month period), the efficacy of the compositions of the invention using vegetal bait surpass 1.000%. The tests conducted in Spain (Almuñécar and Granada) have been implemented on *Rhynchophorus ferrugineus* Olivier, using the feromone and the mixtures provided by this invention, the net results revealing a 560% efficacy over the vegetal reference specimen also provided with its feromone (data not shown).

These results reflect the stability of the insect attracting composition of the invention for the duration of at least one month and capable at all times of emitting the volatile molecules of its components, versus a vegetal bait which normally dries up within 4 to 7 days or rots completely, thus ceasing to emit the precise volatiles.

The results shown in Table 1 (Example 1) furthermore reveal a certain synergic effect deriving from the insect attracting compositions of this invention because of the presence of compounds emitted to a lesser degree from the fermentation of the vegetal material, i.e component (a3).

The insect attracting compositions provided by this invention and their application to insect pest control in plants offer the following advantages:

- longer bait life, thus simplifying the putting into service of the insect control method,
- improved performance, as compared to methods based on entirely vegetal baits,
- increased performance regularity as a result of lower vegetal matter content in the bait, and
- lower costs.

The following example serves to illustrate a particular form of embodiment of the object of this invention, and should not be construed as restrictive of the scope of the invention.

EXAMPLE 1

Study of *Rhynchophorus palmarum* Control in Palm Tree Groves

This experiment was designed to assess the control of *Rhynchophorus palmarum* control in ornamental, palm trees and in coconut palms according to the characteristics indicated hereunder.

Insect species against which the experiment was designed: *Rhynchophorus palmarum, Coleoptera curculionidae*, Rhynchophorinae.

Testing area: Cayenne—Remire Montjoly, French Guiana.

Plants: Ornamental palm tree groves and coconut palms.

Dates: March–May 1997.

Substances tested:

(a) Vegetal bait (sugar cane in 25 cm lengths cut lengthwise through the middle and fermented during 24 hours at 28° C., and Rhynchophorol (synthetic feromone)

(b) INIA 1 composition and Rhynchophorol.

(c) INIA 2 composition and Rhynchophorol.

(c) INIA 3 composition and Rhynchophorol.

(e) Reference specimen (only Rhynchophorol).

| INIA compositions | |
|---|---|
| INIA 1: | Ethyl acetate - 40% |
| | Ethanol - 40% |
| | Ground, stabilized sugar cane - 20% |
| INIA 2: | Ethyl acetate - 35% |
| | Ethanol - 35% |
| | Ground, stabilized sugar cane and coconut fruit, stabilized with ascorbic acid - 25% |
| | Phenol - 2.5% |
| | Acetoin - 2.5% |
| INIA 3: | Ethyl acetate - 35% |
| | Ethanol - 35% |
| | Sugar cane and coconut (same as INIA 2) - 20% |
| | Acetoin - 2.5% |
| | Phenol - 2.5% |
| | Guaiacol - 2.5% |
| | 2-phenylethanol - 2.5% |

TESTING ARRANGEMENT

A randomly selected "double blind" test was repeated 4 times in traps installed over trash cans modified to include spreaders comprising a supporting agent capable of absorbing/adsorbing and releasing the compositions to be tested and designed to emit said compositions.

The vegetal bait, namely cut-up cane, was arranged in a bundle on the bottom of the trap can. Feromone (Rhynchophorol) was released from small hermetic plastic 200 μm envelopes loaded with 0.2 $cm^3$ of synthetic feromone spreading a minimum of 2 mg/day through pores in the trap.

The reference specimen had only the small feromone envelope as an attraction agent. Duration of the test was 1 month.

RESULTS

Overall results are shown in Table 1.

TABLE I

Results for the months of March-April 1997

| Substance tested | Total capture | Daily capture | Total capture |
|---|---|---|---|
| (a) | 72 | 0.6 | 119 |
| (b) | 183 | 1.5 | 312 |
| (c) | 201 | 1.7 | 405 |
| (d) | 218 | 1.8 | 420 |
| (e) | — | — | 3 |

The total capture reflects the total number of insects (*Rhynchophorus palmarum*) trapped in all the traps containing the same test substance.

The daily capture reflects the number of insects (*Rhynchophorus palmarum*) captures per trap/day.

Results obtained reveal not only the efficacy of the attracting compositions provided by the invention but also the synergic effect achieved from including minority compounds—i.e. (a3) component—acetoin, phenol, guaiacol and 2-phenylethanol in said compositions.

What is claimed is:

1. An insect attracting composition, wherein said composition controls insects in plants, said insects being selected from insects of the Coleoptera order, and said plants being selected from plants of the family *Palmaceae*, sugar cane, banana tree, and agaves, said composition comprising:

(1) a mixture comprising the following components:
      (A) a mixture of ethanol and ethyl acetate;
      (B) a vegetable material consisting of sugar cane and coconut meat, said vegetable material being ground, fermented and stabilized with a preserving agent selected from the group consisting of ascorbic acid, citric acid, and mixtures thereof; and
      (C) a mixture of acetoin and phenol; and
   (2) a pheromone; wherein said pheromone is rhynchopherol.

* * * * *